United States Patent
Weir

(10) Patent No.: US 10,779,890 B2
(45) Date of Patent: Sep. 22, 2020

(54) SYSTEM AND METHOD FOR PERFORMING JOINT REPLACEMENT SURGERY USING ARTIFICIAL NEURAL NETWORK

(71) Applicant: Jared Weir, Saginaw, MI (US)

(72) Inventor: Jared Weir, Saginaw, MI (US)

( * ) Notice: Subject to any disclaimer, the term of this patent is extended or adjusted under 35 U.S.C. 154(b) by 0 days.

(21) Appl. No.: 16/362,781

(22) Filed: Mar. 25, 2019

(65) Prior Publication Data

US 2020/0268448 A1 Aug. 27, 2020

Related U.S. Application Data

(60) Provisional application No. 62/811,218, filed on Feb. 27, 2019.

(51) Int. Cl.

| | |
|---|---|
| *A61B 34/10* | (2016.01) |
| *A61B 5/024* | (2006.01) |
| *A61B 5/00* | (2006.01) |
| *G06N 20/00* | (2019.01) |
| *G16H 50/70* | (2018.01) |
| *A61B 34/20* | (2016.01) |
| *G06N 3/08* | (2006.01) |
| *A61B 34/00* | (2016.01) |
| *A61B 34/30* | (2016.01) |
| *A61B 17/17* | (2006.01) |

(52) U.S. Cl.
CPC .............. *A61B 34/10* (2016.02); *A61B 34/20* (2016.02); *A61B 34/25* (2016.02); *A61B 34/30* (2016.02); *G06N 3/08* (2013.01); *A61B 17/17* (2013.01); *A61B 2034/104* (2016.02); *A61B 2034/108* (2016.02); *A61B 2034/2068* (2016.02)

(58) Field of Classification Search
CPC ......... A61B 34/10; A61B 34/30; A61B 34/20; A61B 34/25; A61B 2034/104; A61B 2034/108; A61B 2034/2068; A61B 17/17; G06N 3/08
USPC ....................................................... 706/1–62
See application file for complete search history.

(56) References Cited

U.S. PATENT DOCUMENTS

| 10,166,019 B2 * | 1/2019 | Nawana | G16Z 99/00 |
|---|---|---|---|
| 2016/0070436 A1 * | 3/2016 | Thomas | A61B 6/032 |
| | | | 715/771 |

(Continued)

OTHER PUBLICATIONS

Nemes, S., et al., "Development and validation of a shared decision-making instrument for health-related quality of life one year after total hip replacement based on quality registries data", 2018, Journal of Evaluation in Clinical Practice 24 (2018) 13-21 (Year: 2018).*

(Continued)

*Primary Examiner* — Brandon S Cole

(74) *Attorney, Agent, or Firm* — Carlson, Gaskey & Olds, P.C.

(57) ABSTRACT

This disclosure relates to a system and method for performing joint replacement surgery, and in particular relates to an artificial neural network that uses machine learning to improve patient outcomes. In an example method, the method includes the step of predicting a patient score indicative of a success of a surgical procedure as perceived by a patient using a neural network. Based on the predicted patient score, a surgeon may update a treatment plan in a way that improves the patient's outcome. These and other benefits will be appreciated from the following description.

14 Claims, 3 Drawing Sheets

(56) References Cited

U.S. PATENT DOCUMENTS

| | | | |
|---|---|---|---|
| 2018/0046773 A1* | 2/2018 | Tang | G16H 50/30 |
| 2019/0090969 A1* | 3/2019 | Jarc | A61B 34/25 |
| 2019/0147128 A1* | 5/2019 | O'Connor | G16H 50/70 |
| | | | 703/11 |
| 2020/0138518 A1* | 5/2020 | Lang | A61B 5/05 |
| 2020/0146567 A1* | 5/2020 | Dennis | A61B 5/165 |

OTHER PUBLICATIONS

Peter,W. F. H., "Physiotherapy in hip and knee osteoarthritis: development of a practice guideline concerning initial assessment, treatment and evaluation." 2011,Acta reumatologica portuguesa,Jul. 2011 (Year: 2011).*

* cited by examiner

SYSTEM AND METHOD FOR PERFORMING JOINT REPLACEMENT SURGERY USING ARTIFICIAL NEURAL NETWORK

RELATED APPLICATIONS

This application claims the benefit of U.S. Provisional Application No. 62/811,218, filed Feb. 27, 2019, the entirety of which is herein incorporated by reference.

TECHNICAL FIELD

This disclosure relates to a system and method for performing joint replacement surgery, and in particular relates to an artificial neural network that uses machine learning to improve patient outcomes.

BACKGROUND

A joint replacement is a surgical procedure in which parts of an arthritic or damaged joint are removed and replaced with a prosthesis (i.e., an implant). The prosthesis is designed to replicate the movement of a normal, healthy joint. Joint replacement surgery can be performed on the hip, knee, ankle, wrist, shoulder, and elbow, as examples. Some joint replacement surgeries are assisted by a robot. The robot may assist the surgeon during surgery by allowing the surgeon to make more precise cuts, for example.

SUMMARY

A method according to an exemplary aspect of the present disclosure includes, among other things, predicting a patient score indicative of a success of a surgical procedure as perceived by a patient using a neural network.

In a further non-limiting embodiment of the foregoing method, before the surgical procedure, the step of predicting the patient score is based on at least one of a pre-operative survey and pre-operative data.

In a further non-limiting embodiment of any of the foregoing methods, the method includes using the neural network to recommend an initial surgical plan based on data available before the surgical procedure. The recommended initial surgical plan provides a highest possible predicted patient score as determined by the neural network.

In a further non-limiting embodiment of any of the foregoing methods, the method includes using the neural network to update the predicted patient score during the surgical procedure based on intra-operative data.

In a further non-limiting embodiment of any of the foregoing methods, the method includes using the neural network to recommend an update to a surgical plan during the surgical procedure when the neural network determines that the recommended update to the surgical plan will improve the predicted patient score.

In a further non-limiting embodiment of any of the foregoing methods, the method includes presenting an expected increase to the predicted patient score associated with the recommended update to the surgical plan.

In a further non-limiting embodiment of any of the foregoing methods, an update to the surgical plan is not recommended when the expected increase to the predicted patient score is below a threshold.

In a further non-limiting embodiment of any of the foregoing methods, the method includes using the neural network to recommend a post-operative treatment plan for the patient. The recommended post-operative treatment plan provides a highest possible predicted patient score as determined by the neural network.

In a further non-limiting embodiment of any of the foregoing methods, the method includes training neural network following the surgical procedure based on pre-operative surveys, post-operative surveys, pre-operative data, post-operative data, and intra-operative data associated with the procedure.

In a further non-limiting embodiment of any of the foregoing methods, the surgical procedure is a robot-assisted joint replacement procedure.

In a further non-limiting embodiment of any of the foregoing methods, the step of predicting the patient score is based on at least one of pre-operative surveys, post-operative surveys, pre-operative data, post-operative data, and intra-operative data.

In a further non-limiting embodiment of any of the foregoing methods, the step of predicting the patient score is based on each of pre-operative surveys, post-operative surveys, pre-operative data, post-operative data, and intra-operative data.

In a further non-limiting embodiment of any of the foregoing methods, step of predicting the patient score is based on at least one of temporal data and demographic data of a surgeon.

A robot-assisted surgery system according to an exemplary aspect of the present disclosure includes a neural network configured to predict a patient score indicative of a success of a surgical procedure as perceived by a patient.

In a further non-limiting embodiment of the foregoing robot-assisted surgery system, the system includes a computer system including the neural network, a robotic arm supporting a tool, a camera stand, a guidance cart, and at least one display. The neural network is in electronic communication with each of the robotic arm, the camera stand, the guidance cart, and the at least one display.

In a further non-limiting embodiment of any of the foregoing robot-assisted surgery systems, the neural network is configured to recommend an initial surgical plan based on data available before the surgical procedure. The recommended initial surgical plan provides a highest possible predicted patient score as determined by the neural network.

In a further non-limiting embodiment of any of the foregoing robot-assisted surgery systems, the neural network is configured to update the predicted patient score during the surgical procedure based on intra-operative data, and the neural network is configured to recommend an update to the surgical plan during the surgical procedure when the neural network determines that the recommended update to the surgical plan will improve the predicted patient score.

In a further non-limiting embodiment of any of the foregoing robot-assisted surgery systems, the at least one display presents an expected increase to the predicted patient score associated with the recommended update to the surgical plan.

In a further non-limiting embodiment of any of the foregoing robot-assisted surgery systems, the neural network is configured such that an update to the surgical plan is not recommended when the expected increase in the predicted patient score is below a threshold.

In a further non-limiting embodiment of any of the foregoing robot-assisted surgery systems, the neural network is configured to recommend a post-operative treatment plan for the patient. The recommended post-operative treatment plan provides a highest possible predicted patient score as determined by the neural network.

DETAILED DESCRIPTION

Again, this disclosure relates to a system and method for performing joint replacement surgery, and in particular relates to an artificial neural network that uses machine learning to improve patient outcomes. In an example method, the method includes the step of predicting a patient score indicative of a success of a surgical procedure as perceived by a patient using a neural network. Based on the predicted patient score, a surgeon may update a treatment plan in a way that improves the patient's outcome. These and other benefits will be appreciated from the following description.

Figure 1:
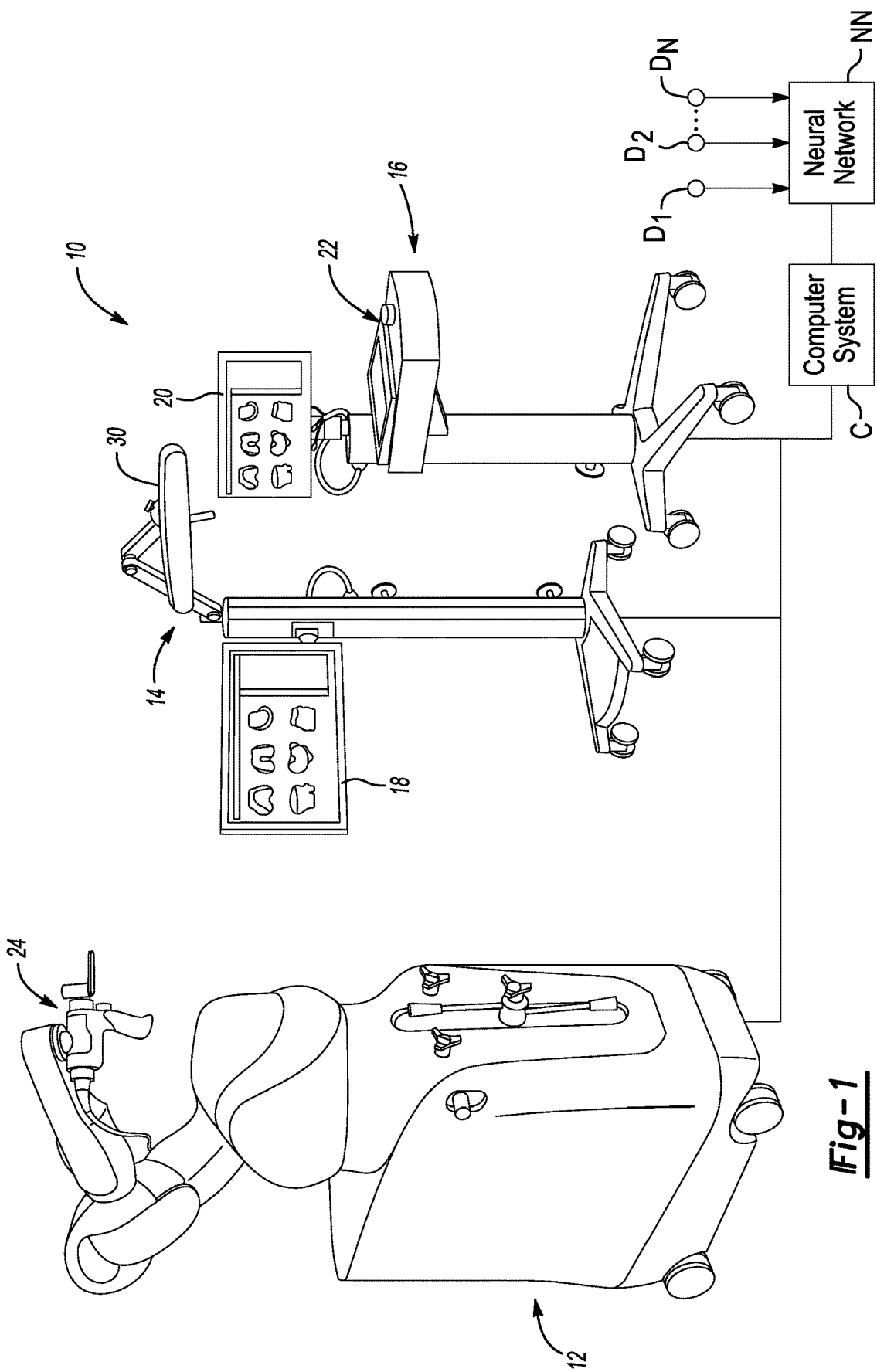
FIG. 1 schematically illustrates an example system.

FIG. 1 schematically illustrates an example robot-assisted orthopedic surgery system 10 ("system 10"). The system 10 is configured to assist a surgeon in performing robot-assisted total joint replacements, such as total knee replacements (i.e., total knee arthroplasties) or partial knee replacements.

In this example, the system 10 includes a robotic arm 12, a camera stand 14, and a guidance cart 16. The camera stand 14 includes a display 18. Further, the guidance cart 16 includes a computer and a user interface including a display 20 and user inputs 22 such as a mouse and keyboard. While three components (i.e., the robotic arm 12, camera stand 14, and guidance cart 16) are shown in FIG. 1, it should be understood that these components are examples only, and the system 10 may be comprised of other types of components.

The various components of the system 10 are electronically connected together and are configured to send and receive information to and from one another. To this end, the system 10 includes a computer system C, which is shown schematically in FIG. 1 and is representative of a known computer system including a combination of hardware devices, software programs, processors, memory, etc. The computer system C may be embodied as a single device or a combination of devices, including servers. The computer system C may have components mounted to the robotic arm 12, camera stand 14, and guidance cart 16 in one example.

Figure 2:
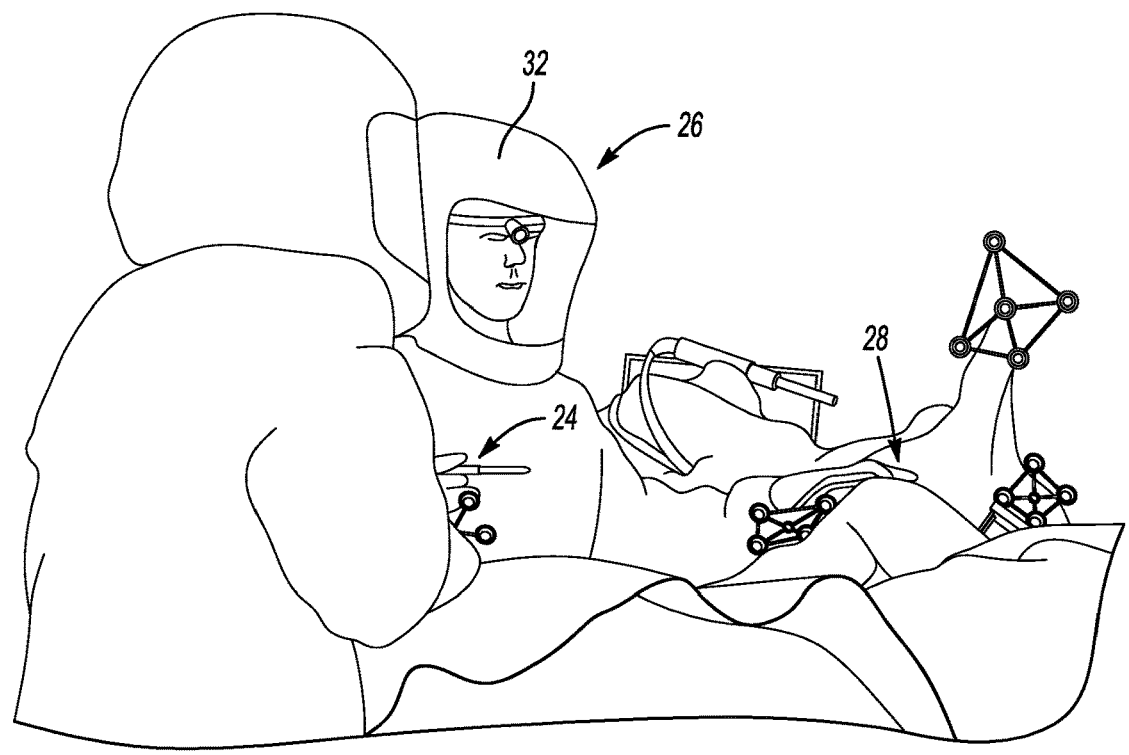
FIG. 2 illustrates a surgeon relative to a patient. The surgeon is performing a robot-assisted joint replacement surgery using the example system.

The robotic arm 12 includes a tool 24 at an end thereof, which is selectively positioned in three-dimensional space and operable by a surgeon 26 (FIG. 2) relative to a patient 28 during surgery. The tool 24 may be any known type of surgical device used in a total or partial joint replacement surgery. In one example, the tool 24 is a saw and has a known spatial relationship relative to a number of positioning markers. The system 10 is configured to determine the position of the tool 24 and the patient 28 in three-dimensional space using information from the camera stand 14, for example.

To this end, the camera stand 14 may include one or more position measuring systems, including, for example, at least one camera 30 that is in communication with a computer system C and positioned to detect light reflected from a number of light reflecting markers on the tool 24. The camera stand 14 is further configured to determine and track the position of the bones of the patient 28, such as the patient's femur and tibia in the case of a total or partial knee replacement. The tracked objects, including the tool 24 and the patient's bones, can be displayed on one or more of the displays 18, 20.

Figure 3:
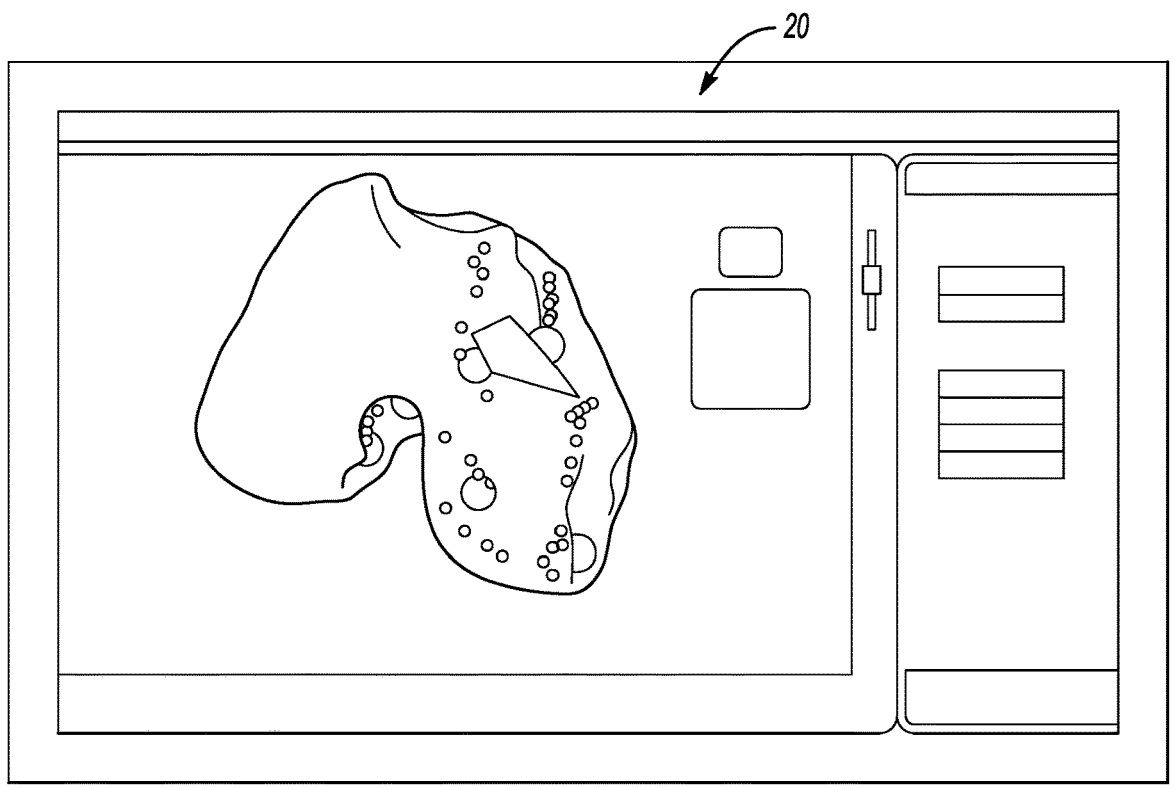
FIG. 3 is representative of a display of the example system.

During surgery, the surgeon 26 may grasp the tool 24, move it in space and use it to perform cuts, etc., using feedback from the system 10. The computer system C interprets information gathered from the system 10 and allows the surgeon 26 to use that information during surgery. The computer system C has access to data such as medical imaging data, ultrasound data, etc., which may be used in planning the position and path of the tool 24 during various steps of a surgical procedure. Example information displayed to the surgeon 26 during a procedure is shown on the display 20 in FIG. 3.

The success of an orthopedic procedure such as a joint replacement depends on a number of factors, one of which is the patient's perceived success of the procedure. The patient's perceived success of the procedure depends on a number of factors, some of which are objective (e.g., the patient's BMI, height, weight, etc.), and some of which are subjective, such as the patient's overall demeanor and attitude toward life. For instance, a high performance athlete with an overall positive disposition will likely perceive the success of a surgical procedure differently one year following the procedure than a patient that engages in minimal physical activity and exhibits an overall negative attitude.

This disclosure quantifies the patient's perceived success of the procedure as a "patient score." The patient score is a prediction on a number scale, such as on a scale of 0 to 100, with 100 being a perfect score. The scale may be an industry standard scale, such as a knee injury osteoarthritis outcome score (KOOS), Oxford Knee Score, Knee Society Score, or a Forgotten Knee Score. In general, this disclosure considers data from a plurality of sources, including real-time surgical data, and predicts the patient score based on that data. The patient score may correlate to the predicted success of the surgery one year following the operation, in one example.

While surgeons are certainly trained to provide successful outcomes for their patients, there are practical limitations on the amount of data a human can process. Some data may not be deemed important, for example, but upon reflection, and in combination with other available factors, including subjective factors, that data could have been used by the surgeon to adjust their surgery strategy to improve a patient score. In other words, some data may present itself either pre-surgery or during surgery as either meaningless or irrelevant when in reality that data would have been useful and informative for a particular patient.

Accordingly, in this disclosure, the system 10 includes an artificial neural network NN ("neural network NN;" FIG. 1) in electronic communication with the system 10. The neural network NN may be incorporated in or interfaced with the computer system C. Alternatively or in addition, the neural network NN may be embodied in whole or in part on a cloud based service.

The neural network NN is configured to receive and process a plurality of different types of data $D_1$-$D_N$, where "N" represents any number. The neural network NN may be a deep generative neural network, which is alternatively referred to as a flow model neural network. The neural network NN provides a framework for machine learning. Specifically, the neural network NN is trained to predict how various data inputs (i.e., from the data $D_1$-$D_N$) relate to patient score. The neural network NN then reports whether it has identified data that may affect the patient score, either positively or negatively, and makes a recommendation regarding whether the surgeon 26 should adjust a surgical plan. This will now be explained in more detail relative to FIG. 4.

Before getting to the details of the method 100 of FIG. 4, several example types of data $D_1$-$D_N$ available to the neural network NN will now be described. The below discussion of data is exemplary and non-limiting. This neural network NN may consider other types of data.

A first category of data is pre-operative data. Such data includes pre-operative patient surveys that evaluate the patient's condition, demeanor, attitude, expectations for surgery, lifestyle, overall health, life and health goals, etc. One such survey is known as the Patient-Reported Outcomes Measurement Information System (PROMIS). The data also includes medical imaging such as MRI, CT scans, or X-ray scans. The pre-operative data also includes data pertaining to implants that may be used during surgery. Such data includes the implant type, material type, size, whether use of the implant requires removal of ligaments, etc. Another source of pre-operative data is derived from sensors worn by the patient during a pre-surgery physical assessment of the patient. Such sensors are used to assess the patient's range of motion, among other things, and may be indicative of the ultimate success of the procedure. Example sensors are the Claris Reflex or the TracPatch. Other sources of pre-operative data include clinical notes including written electronic text, for example, and charts including measurements taken by a surgeon for range of motion and angular deformity of a limb.

A second category of data is intra-operative data. This category of data is real-time surgical data pertaining to the particular surgical procedure that is being performed. Such data may be derived from any of the components of the system 10, including robotic data derived from the robotic arm 12 and/or the camera stand 14. The data also includes intra-operative medical imaging such as CT or X-ray scans. Intra-operative data may also include data from sensors, such as load sensors, used during surgery. Further, the data may include data from a helmet 32 (FIG. 2) worn by a surgeon 26 during the procedure. An example helmet 32 is a Flyte helmet offered commercially by Stryker Corporation. The helmet 32 may include a voice recorder configured to record the surgeon's voice during a procedure. The commands and/or notes orally dictated by the surgeon 26 during the procedure are examples of data fed to the neural network NN. The neural network NN may be configured to interpret the surgeon's oral dictations (e.g., "please hand me the scalpel," "I have released the MCL") and determine the stage of the procedure. Other types of data include monitor data, which is data pulled from a monitor, such one of the displays 18, 20 or a DVI monitor, during a procedure.

A third category of data is post-operative data. Such data includes post-operative patient surveys. One such survey is the PROMIS survey, which may be given to the patient both before and after surgery. Another source of post-operative data is derived from sensors worn by the patient during physical therapy, for example. Again, example sensors are the Claris Reflex or the TracPatch. Yet another source of post-operative data is hospital reported outcome (HRO) data, which may include how long the patient stayed in the hospital or rehab facility, for example, following a procedure, and further includes information such as their medications, the nature of their stay, their pain level, the range of motion the patient exhibited during their stay, etc. Clinical notes, such as those from a surgeon or physical therapist, are another possible source of post-operative data. To this end, the patient's attendance record at physical therapy sessions is also a source of data.

Figure 4:
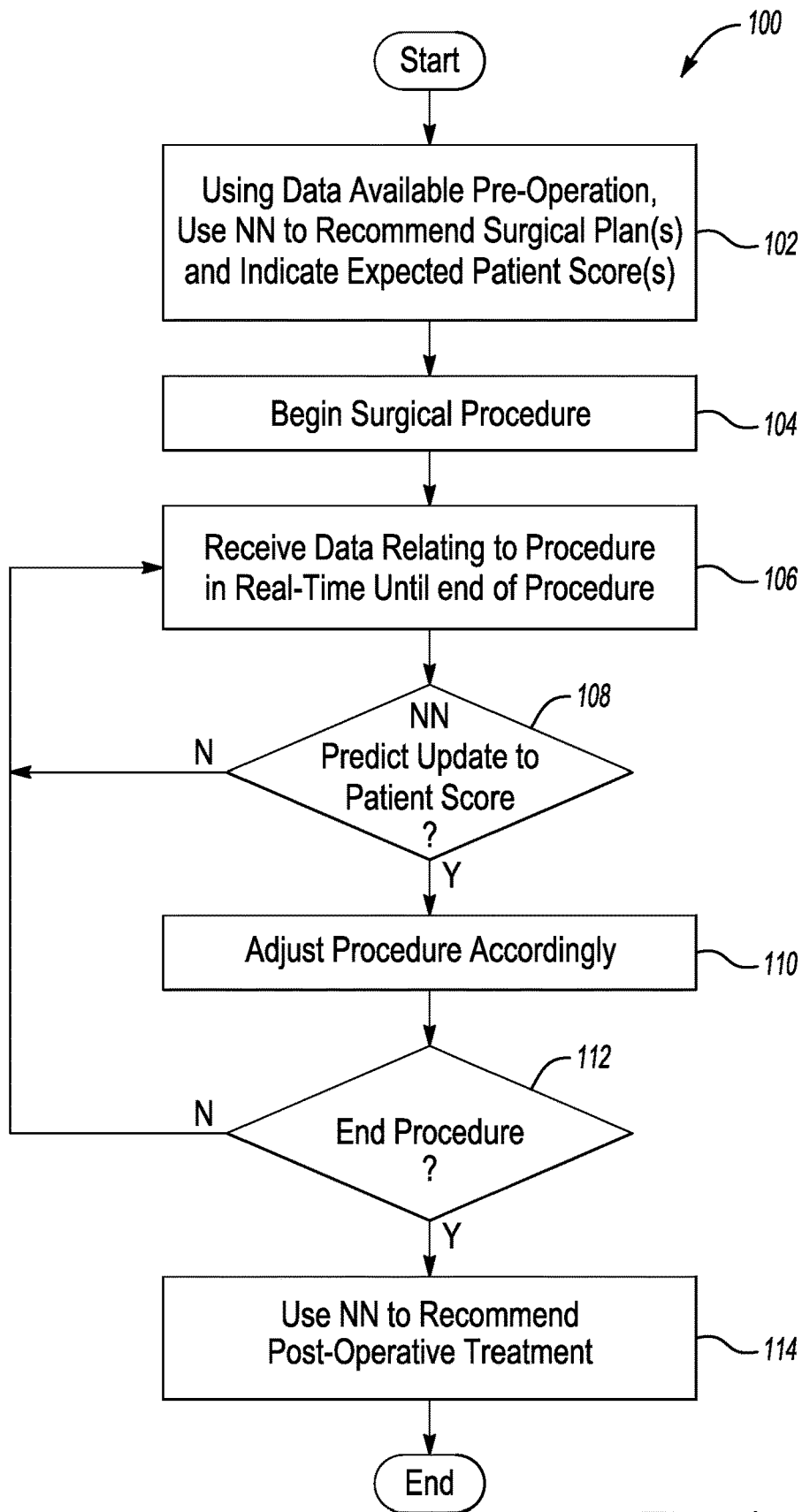
FIG. 4 is a flow chart representative of a method of this disclosure.

FIG. 4 is a flow chart representative of an example method 100 according to this disclosure. Before beginning the method 100, however, the neural network NN is trained to predict patient scores based on data from previous surgical procedures. The data from the previous surgical procedures includes pre-operative surveys, post-operative surveys, pre-operative data, post-operative data, and intra-operative data, etc. Over time, the neural network NN is trained to relate this data to a patient score.

With the neural network NN initially trained, the method 100 begins. It should be noted that the neural network NN is continually trained as the neural network NN is used. In other words, training does not stop after the initial training. Thus, over time, the neural network NN makes more accurate and useful predictions regarding how certain data relates to patient score.

The method 100 begins before a surgical procedure. For purposes of explanation, the method 100 will be described relative to a knee replacement procedure, although it could apply to shoulder replacements, hip replacements, etc.

At 102, the neural network NN assesses all available pre-operative data, such as that discussed above, and makes recommendations to the surgeon 26 regarding the surgical plan. In particular, the neural network NN may indicate that a particular type of implant should be used in the procedure. The neural network NN may provide a list of options for implant types and indicate how those options will affect the patient score. To be clear, the term "recommend" or "recommendation" as it relates to the neural network NN is not intended to imply that the neural network NN is making medical decisions. Rather, the neural network NN uses statistical analysis and probabilities to outline options, or recommendations, that a person with a medical license, such as the surgeon 26, may follow at their discretion.

The neural network NN may also recommend that the surgeon 26 perform a particular procedure in a particular way. The neural network NN, for example, may recommend that the surgeon 26 perform a partial knee replacement as opposed to a total knee replacement. This aspect of the disclosure is particularly beneficial because, in today's age, total knee replacements have become the default surgery option because of the difficulty in identifying good candidates for partial knee replacement surgeries. The neural network NN, using all of the data available to it, helps surgeons identify good candidates for partial knee replacements, which is a less invasive procedure and produces better results for the right candidates.

The neural network NN may indicate how each option (i.e., total knee or partial knee replacement) will affect the patient score. The neural network NN may also suggest a number of steps for the surgeon 26 to perform and an order to those steps. The surgeon 26 may use their discretion to accept or decline the recommendations of the neural network NN using an interface, such as that on the guidance cart 16.

With the surgical plan set, the procedure begins at 104. At 106, the neural network NN receives all intra-operative data, such as that discussed above. As the neural network NN receives the incoming intra-operative data, the neural network NN updates the patient score, at 108, and the system 10 relays that information to the surgeon 26. The neural network NN also continues to reevaluate the surgical plan and, at 110, considers whether an adjustment to the surgical plan will affect the patient score. If the neural network NN identifies a possible change in the surgical plan that will increase the patient's score, the neural network NN relays that information to the surgeon 26 via the system 10 so that the surgeon 26 can act on the information, at their discretion.

As one example, there are practical limitations to pre-operative CT scans and X-ray scans. Thus, when a surgeon 26 opens a patient's knee for surgery, more details of the patient's anatomy may become apparent. For instance, a bone spur or other bone defect may be visible after opening the patient's knee whereas the same was not identifiable on a pre-operative CT scan. With the knowledge of the additional details of the anatomy, the neural network NN may recommend a change to the surgical plan that it predicts will increase the patient score. The system 10 will present that recommendation and the corresponding expected increase in patient score to the surgeon 26 (i.e., "remove bone spur for a 3 point increase in patient score?"), and the surgeon 26 can choose to follow the recommendation at their discretion.

In this respect, when a change to the surgical plan will only increase the patient score marginally, the surgeon 26 can weigh that relatively small increase against the drawbacks of changing the surgical plan mid-surgery. Over time, the neural network NN can be trained such that it only presents options that significantly improve patient score. Alternatively or in addition, the neural network NN can present the surgeon 26 with all options for updating the surgical plan.

As another example of adjusting the surgical procedure intra-operatively, the neural network NN may consider kinematic data regarding how the knee is moving and how the soft tissues are reacting during the procedure. In particular, the neural network NN may use this kinematic data, in combination with a CT scan (which is a static image), to recommend changes in a surgical procedure such as changing an implant type to one that does not require particularly strong ligaments (e.g., if the kinematic data indicates the ligaments are not particularly healthy or strong). Alternatively or in addition, the neural network NN may recommend a change in implant location. Further still, the neural network NN could recommend a ligament lengthening procedure.

As yet another example, the neural network NN could use intra-operative data from a load sensor to recommend adjustments to the virtual placement of the implants before a surgeon performs actual cuts. The neural network NN can predict whether a recut after an original cut would increase patient score. The surgeon 26 could, for example, make an oral request to the neural network NN, such as by stating aloud, "what is the most efficient next step?" The neural network NN would then respond, via the computer system C, with a recommended next step, such as the next recommended cut location.

As still another example, the neural network NN may consider temporal data and demographic data. Such data may include time of day, the surgeon's schedule and/or workload, the handedness of the surgeon (i.e., is the surgeon right-handed or left-handed), etc. The neural network NN may compare that data with the other types of data discussed above. As an illustrative example, the neural network NN may be able to make predictions that account for the predicted fatigue of the surgeon. For instance, if a surgeon is operating on a relatively large patient late in the day on a Friday, while performing a particular step using their off-hand, the neural network NN may predict that the surgeon's performance of that step will be influenced by fatigue. This aspect of the disclosure may be particularly relevant in the context of gap measurements between bones, because the surgeon 26 has to apply a physical load to distract the joints. The neural network NN can take into account the surgeon's predicted fatigue is it relates these measurements and other surgical steps.

There are additional examples where the neural network NN will use intra-operative data to recommend updates to the surgical plan to improve the patient score. In fact, the beauty of this disclosure is that it is not possible to predict all the ways the neural network NN may react to certain combinations of data. That is, as the neural network NN continues its machine learning process, the neural network NN may make recommendations that are not possible to predict today but ultimately benefit the patient. This is in part because the neural network NN makes its recommendations based on both subjective and objective data that are personal to each patient and each patient's perceived success of the particular operation.

The neural network NN continues updating the patient score throughout the surgery. Continually updating the patient score helps the surgeon evaluate whether particular steps have been performed successfully. For instance, if the patient score holds constant or increases during a particular step, the surgeon knows that the step was performed successfully.

Steps 106, 108, and 110 continue until the procedure ends, at 112. Following the procedure, the neural network NN, at 114, may recommend post-operative treatment options for the patient. For instance, based on the data received during the procedure combined with the pre-operative data, the neural network NN may conclude that the procedure was a success and that prolonged physical therapy would not benefit the patient. Accordingly, the information from the neural network NN can save the patient copays on their insurance they would otherwise pay for additional physical therapy sessions. The neural network NN may make additional recommendations regarding post-operative treatments. Further, as mentioned above, the neural network NN receives post-operative data, such as that discussed above, so that the neural network NN can verify whether its predictions in patient score were ultimately correct, and, in turn, continue learning over time, leading to even better patient scores.

Although the different examples have the specific components shown in the illustrations, embodiments of this disclosure are not limited to those particular combinations. It is possible to use some of the components or features from one of the examples in combination with features or components from another one of the examples. In addition, the various figures accompanying this disclosure are not necessarily to scale, and some features may be exaggerated or minimized to show certain details of a particular component or arrangement.

One of ordinary skill in this art would understand that the above-described embodiments are exemplary and non-limiting. That is, modifications of this disclosure would come within the scope of the claims. Accordingly, the following claims should be studied to determine their true scope and content.

The invention claimed is:

1. A method, comprising:
   predicting a patient score indicative of a success of a surgical procedure as perceived by a patient using a neural network, wherein the step of predicting the patient score is based on a predicted fatigue of a surgeon, and wherein the predicted fatigue of the surgeon is based on each of a time of day, a schedule of the surgeon, a workload of the surgeon, and a handedness of the surgeon;

using the neural network, updating the predicted patient score during the surgical procedure based on the predicted fatigue of the surgeon;

using the neural network, accounting for the predicted fatigue of the surgeon during the surgical procedure when evaluating gap measurements between bones, wherein the gap measurements are obtained when the surgeon applies a physical load to distract a joint;

using the neural network, recommending an update to a surgical plan during the surgical procedure when the neural network determines, based on the predicted fatigue of the surgeon, that the recommended update to the surgical plan will improve the predicted patient score; and presenting, to the surgeon during the surgical procedure, an expected increase to the predicted patient score associated with the recommended update to the surgical plan.

2. The method as recited in claim 1, wherein, before the surgical procedure, the step of predicting the patient score is based on at least one of a pre-operative survey and pre-operative data.

3. The method as recited in claim 2, further comprising: using the neural network, recommending an initial surgical plan based on data available before the surgical procedure, wherein the recommended initial surgical plan provides a highest possible predicted patient score as determined by the neural network.

4. The method as recited in claim 3, further comprising: using the neural network, recommending a post-operative treatment plan for the patient, wherein the recommended post-operative treatment plan provides a highest possible predicted patient score as determined by the neural network.

5. The method as recited in claim 1, wherein an update to the surgical plan is not recommended when the expected increase to the predicted patient score is below a threshold.

6. The method as recited in claim 3, further comprising: training neural network following the surgical procedure based on pre-operative surveys, post-operative surveys, pre-operative data, post-operative data, and intra-operative data associated with the procedure.

7. The method as recited in claim 1, wherein the surgical procedure is a robot-assisted joint replacement procedure.

8. The method as recited in claim 1, wherein the step of predicting the patient score is based on at least one of pre-operative surveys, post-operative surveys, pre-operative data, post-operative data, and intra-operative data.

9. The method as recited in claim 8, wherein the step of predicting the patient score is based on each of pre-operative surveys, post-operative surveys, pre-operative data, post-operative data, and intra-operative data.

10. A robot-assisted surgery system, comprising:
a neural network configured to predict a patient score indicative of a success of a surgical procedure as perceived by a patient, wherein the neural network is configured to predict the patient score based on a predicted fatigue of a surgeon, and wherein the predicted fatigue of the surgeon is based on each of a time of day, a schedule of the surgeon, a workload of the surgeon, and a handedness of the surgeon, wherein the neural network is configured to update the predicted patient score during the surgical procedure based on the predicted fatigue of the surgeon, wherein the neural network is configured to account for the predicted fatigue of the surgeon during the surgical procedure when evaluating gap measurements between bones, wherein the gap measurements are obtained when the surgeon applies a physical load to distract a joint, wherein the neural network is configured to recommend an update to a surgical plan during the surgical procedure when the neural network determines, based on the predicted fatigue of the surgeon, that the recommended update to the surgical plan will improve the predicted patient score; and at least one display, wherein the neural network is configured to cause the at least one display to display, to the surgeon during the surgical procedure, an expected increase to the predicted patient score associated with the recommended update to the surgical plan.

11. The robot-assisted surgery system as recited in claim 10, further comprising:
a computer system including the neural network;
a robotic arm supporting a tool;
a camera stand;
a guidance cart; and
wherein the neural network is in electronic communication with each of the robotic arm, the camera stand, the guidance cart, and the at least one display.

12. The robot-assisted surgery system as recited in claim 11, wherein the neural network is configured to recommend an initial surgical plan based on data available before the surgical procedure, wherein the recommended initial surgical plan provides a highest possible predicted patient score as determined by the neural network.

13. The robot-assisted surgery system as recited in claim 10, wherein the neural network is configured such that an update to the surgical plan is not recommended when the expected increase in the predicted patient score is below a threshold.

14. The robot-assisted surgery system as recited in claim 10, wherein the neural network is configured to recommend a post-operative treatment plan for the patient, and wherein the recommended post-operative treatment plan provides a highest possible predicted patient score as determined by the neural network.

* * * * *